(12) United States Patent
Coates

(10) Patent No.: US 7,339,657 B2
(45) Date of Patent: Mar. 4, 2008

(54) LOW-COST ON-LINE AND IN-LINE SPECTRAL SENSORS BASED ON SOLID-STATE SOURCE AND DETECTORS COMBINATIONS FOR MONITORING LUBRICANTS AND FUNCTIONAL FLUIDS

(75) Inventor: John Coates, Newtown, CT (US)

(73) Assignee: Sentelligence, Inc., Noblesville, IN (US)

( * ) Notice: Subject to any disclaimer, the term of this patent is extended or adjusted under 35 U.S.C. 154(b) by 348 days.

(21) Appl. No.: 10/492,660

(22) PCT Filed: Oct. 11, 2002

(86) PCT No.: PCT/US02/32621

§ 371 (c)(1),
(2), (4) Date: Apr. 10, 2004

(87) PCT Pub. No.: WO03/030621

PCT Pub. Date: Apr. 17, 2003

(65) Prior Publication Data

US 2004/0201835 A1    Oct. 14, 2004

Related U.S. Application Data

(60) Provisional application No. 60/328,885, filed on Oct. 11, 2001.

(51) Int. Cl.
*G01N 21/17* (2006.01)
(52) U.S. Cl. .................. 356/73; 356/417; 356/436; 250/458.1; 250/339.12; 250/343
(58) Field of Classification Search ............ 356/73, 356/417, 436
See application file for complete search history.

(56) References Cited

U.S. PATENT DOCUMENTS 2,649,011 A   8/1953   Black (Continued)

FOREIGN PATENT DOCUMENTS

EP    0206433 A2    12/1986

(Continued)

OTHER PUBLICATIONS

Coates et al, The Analytical and Satistical Evaluation of Infrared Spectroscopic Data from Used Diesel Lubricants, SAE Fuels and Lubricants Meeting, Oct., 1984.

*Primary Examiner*—F. L. Evans
(74) *Attorney, Agent, or Firm*—David Aker

(57) ABSTRACT

A series of optical spectral sensors is based on a combination of solid-state sources (illumination) and detectors housed within an integrated package that includes the interfacing optics and acquisition and processing electronics. The focus is on low cost and the fabrication of the sensor is based on techniques that favor mass production. Materials and components are selected to support low-cost, high volume manufacturing of the sensors. Spectral selectivity is provided by the solid-state source(s) thereby eliminating the need for expensive spectral selection components. The spectral response covers the range from the visible (400 nm) to the mid-infrared (25,000 nm/25.0 µm), as defined by the availability of suitable low-cost solid-state source devices. A refractive optical system is employed, primarily in an internal reflection mode, allowing a selection of sample handling tools, including, but not restricted to internal reflectance and transmittance. A secondary channel allowing for light scattering or fluorescence methods is an option. The targeted applications of the sensing devices are for lubricants and functional fluids in the heavy equipment, automotive and transportation industries. A source reference channel is included to provide measurement stability and temperature compensation.

36 Claims, 9 Drawing Sheets

U.S. PATENT DOCUMENTS

| | | | |
|---|---|---|---|
| 3,364,812 A | 1/1968 | Ewing | |
| 3,370,502 A | 2/1968 | Wilks, Jr. | |
| 3,460,893 A | 8/1969 | Wilks, Jr. | |
| 3,508,830 A | 4/1970 | Hopkins et al. | |
| 3,578,865 A | 5/1971 | Traver | |
| 3,619,072 A | 11/1971 | O'Hara et al. | |
| 3,665,201 A | 5/1972 | Shea et al. | |
| 3,713,743 A | 1/1973 | Simms | |
| 3,714,444 A | 1/1973 | Carr et al. | |
| 3,734,629 A | 5/1973 | Griffiths et al. | |
| 3,790,279 A | 2/1974 | Skala | |
| 3,876,307 A | 4/1975 | Skala | |
| 3,892,485 A | 7/1975 | Merritt et al. | |
| 4,441,971 A | 4/1984 | Ishiguro et al. | |
| 4,570,069 A | 2/1986 | Gager | |
| 4,595,833 A | 6/1986 | Sting | |
| 4,649,711 A | 3/1987 | Sibley et al. | |
| 4,699,509 A | 10/1987 | Kamiya et al. | |
| 4,701,838 A | 10/1987 | Swinkels et al. | |
| 4,975,581 A | 12/1990 | Robinson et al. | |
| 5,000,569 A | 3/1991 | Nylund | |
| 5,021,665 A | 6/1991 | Ames | |
| 5,049,742 A | 9/1991 | Hosonuma et al. | |
| 5,050,946 A | 9/1991 | Hathaway et al. | |
| 5,051,551 A | 9/1991 | Doyle | |
| 5,071,527 A | 12/1991 | Kauffman | |
| 5,076,397 A | 12/1991 | Yamada | |
| 5,077,477 A | 12/1991 | Stroman et al. | |
| 5,089,780 A | 2/1992 | Megerle | |
| 5,125,742 A | 6/1992 | Wilks, Jr. | |
| 5,185,640 A | 2/1993 | Wilks, Jr. et al. | |
| 5,196,898 A | 3/1993 | Tamura et al. | |
| 5,278,426 A * | 1/1994 | Barbier | 250/577 |
| 5,296,843 A | 3/1994 | Wohlstein et al. | |
| 5,407,830 A | 4/1995 | Altman et al. | |
| 5,438,420 A | 8/1995 | Harwick et al. | |
| 5,440,126 A | 8/1995 | Kemsley | |
| 5,442,435 A * | 8/1995 | Cooper et al. | 356/133 |
| 5,452,083 A | 9/1995 | Wilks, Jr. | |
| 5,534,708 A * | 7/1996 | Ellinger et al. | 250/577 |
| 5,548,393 A | 8/1996 | Nozawa et al. | |
| 5,608,518 A | 3/1997 | Wilks, Jr. | |
| 5,691,701 A | 11/1997 | Wohlstein et al. | |
| 5,739,916 A | 4/1998 | Englehaupt | |
| 5,741,961 A | 4/1998 | Martin et al. | |
| 5,790,246 A | 8/1998 | Kuhnell et al. | |
| 5,798,452 A | 8/1998 | Martin et al. | |
| 5,889,683 A | 3/1999 | Ismail et al. | |
| 5,939,727 A | 8/1999 | Sommer | |
| 6,040,578 A * | 3/2000 | Malin et al. | 250/339.12 |
| 6,043,505 A | 3/2000 | Ames et al. | |
| 6,049,088 A | 4/2000 | Harding | |
| 6,091,484 A | 7/2000 | Venica et al. | |
| 6,118,520 A * | 9/2000 | Harner | 356/73 |
| 6,151,108 A | 11/2000 | Kwon et al. | |
| 6,331,704 B1 | 12/2001 | Owen | |
| 6,388,251 B1 * | 5/2002 | Papanyan | 250/269.1 |
| 6,420,708 B2 | 7/2002 | Wilks, Jr. et al. | |
| 6,690,452 B2 | 2/2004 | Wilks, Jr. | |
| 2002/0069021 A1 | 6/2002 | Takezawa et al. | |

FOREIGN PATENT DOCUMENTS

| | | |
|---|---|---|
| EP | 0797091 A1 | 9/1997 |
| EP | 0836092 A2 | 4/1998 |
| GB | 2346691 A | 8/2000 |
| JP | 63266342 | 11/1966 |
| JP | 57142546 | 9/1982 |
| JP | 60111946 | 6/1985 |
| JP | 08201278 | 8/1986 |
| JP | 61213749 | 9/1986 |
| JP | 02259548 | 10/1990 |
| JP | 03-111741 | 5/1991 |
| JP | 3142349 | 6/1991 |
| JP | 07280720 | 10/1995 |
| JP | 08-062207 | 3/1996 |
| KR | 0150054 | 12/1998 |
| WO | WO88/03109 | 3/1988 |

OTHER PUBLICATIONS

A. M. Toms, Preliminary Report on the Evaluation of FTIR for Lubricant Condit and Contamination determination in Support of Machinary Condition Monitoring. I. Synthetic Lubticants, Joint Oil Analysis Program (approx. 1999).

Coates et al., A Rapid Field-Based method for the Determination of Soot in Used Diesel Oils, P/PM Technology, vol. 9, No. 6, Dec., 1996 pp. 30-34.

D.L. Wooton, Applications of Spectroscopy in the Fuels and Lubrication Industry Applied Spectroscopy Reviews, vol. 36, No. 4, pp. 315-332 (2001).

LEM® Safeguards Against Diesel Fuel, Analyst, Inc., (1995 to 2000 and Oct. 2002) 4 pages total.

Standard Practice for Condition Monitoring of Used Lubricant using Fourier Transform Infrared (FT-IR) Spectrometry, ASTM Draft Method (Oct. 4, 2002).

* cited by examiner

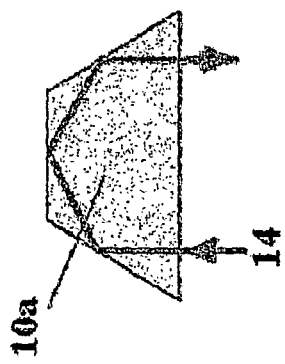
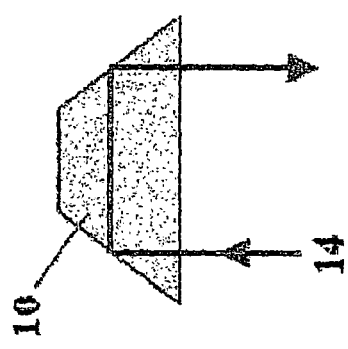
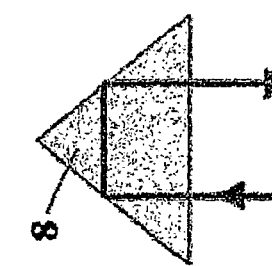
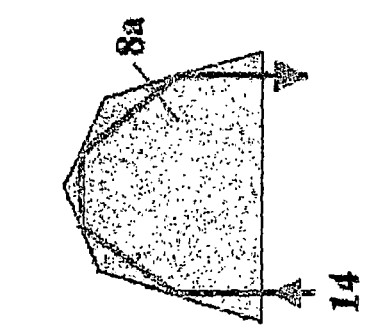
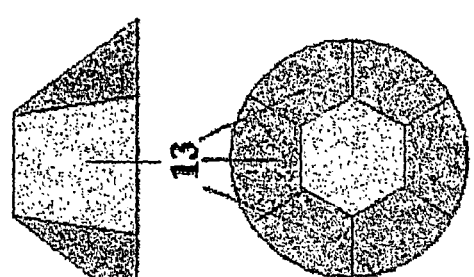
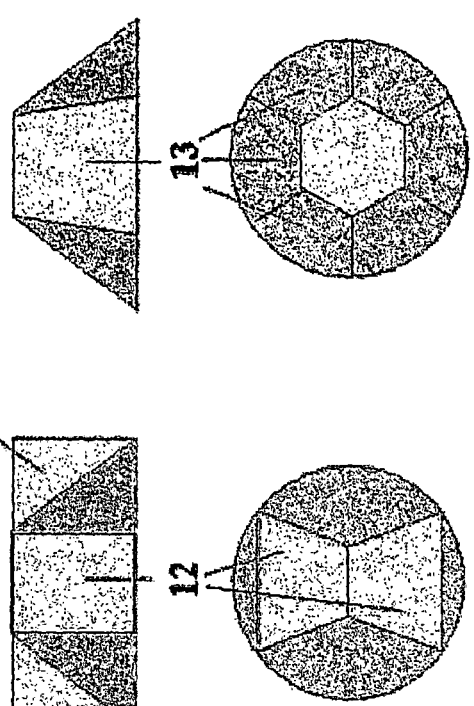
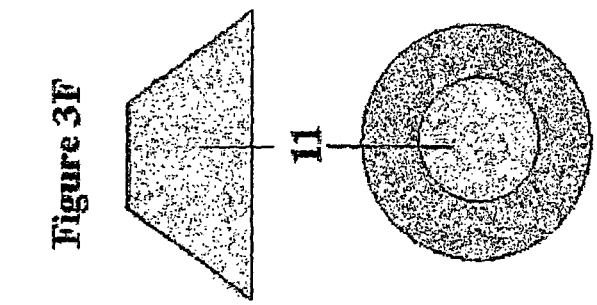
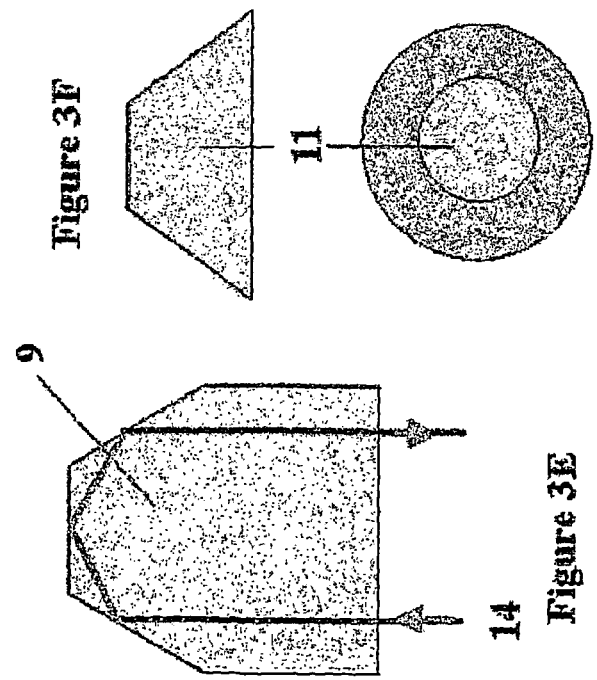

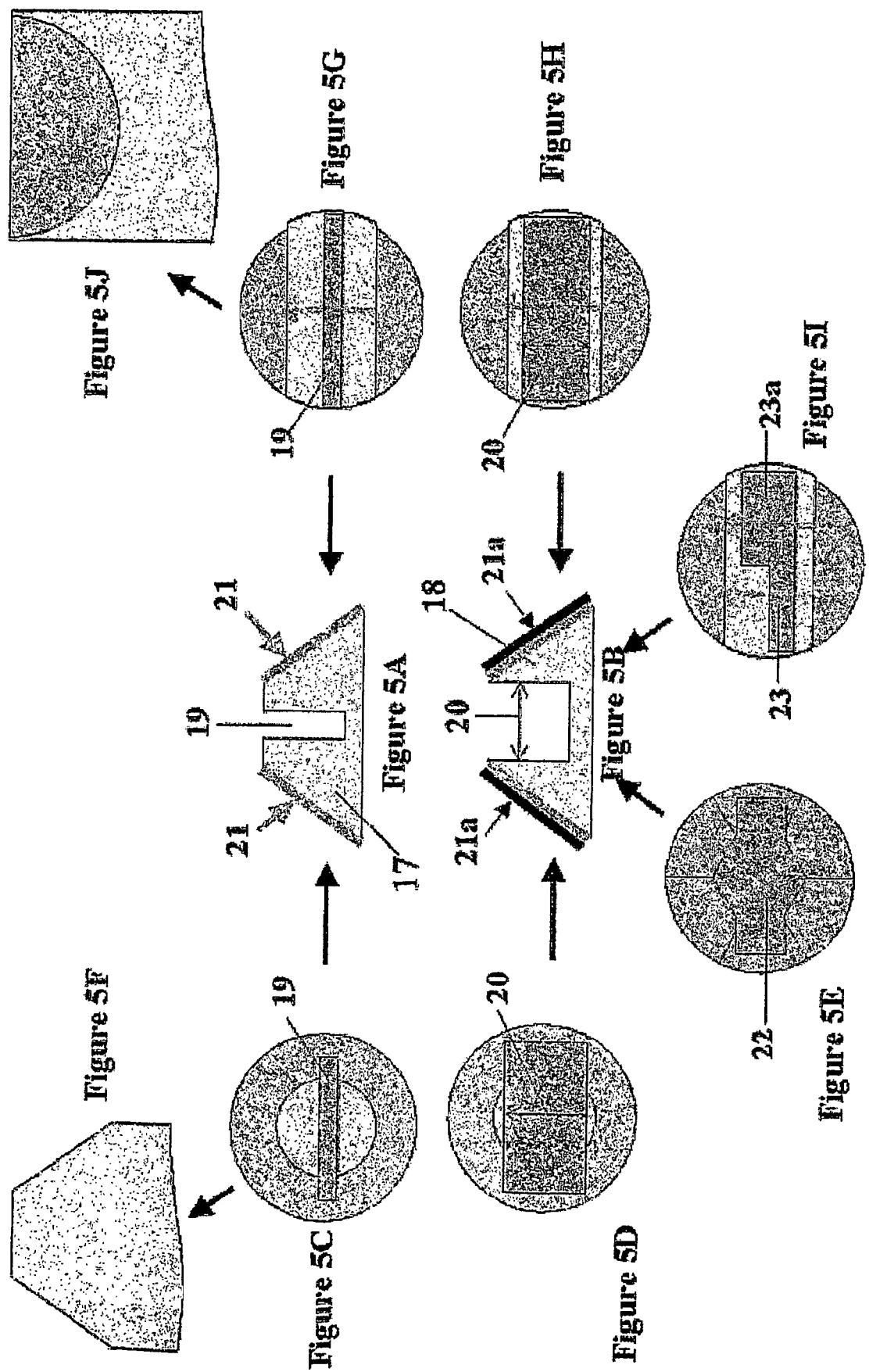

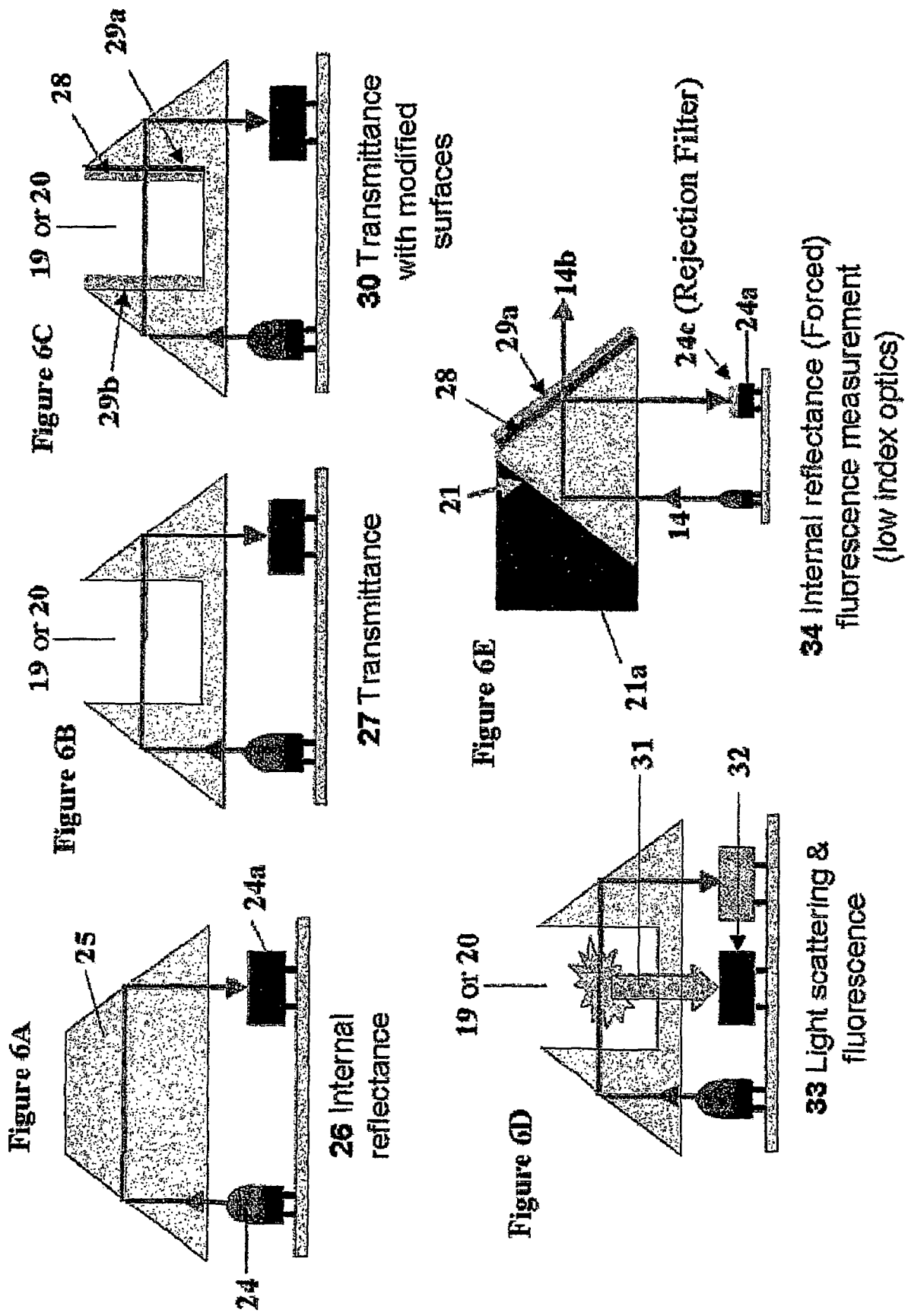

39 LED/Detector combo with light conduit

37 LED/detector combo with fiber-optic coupling

35 Simple LED/detector combination

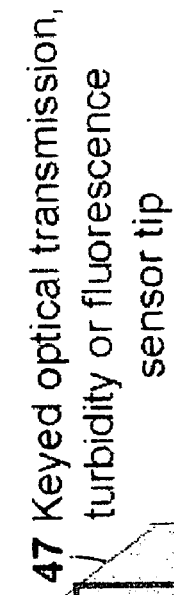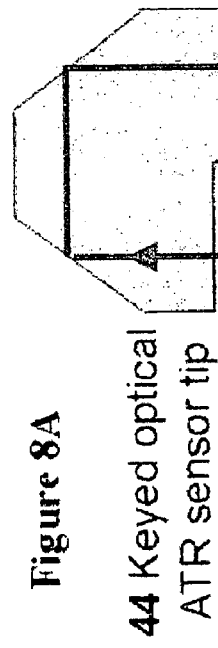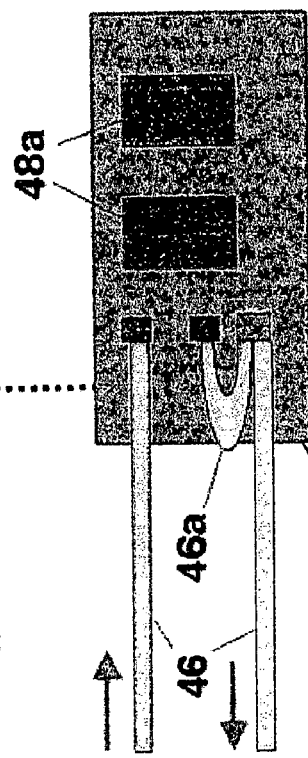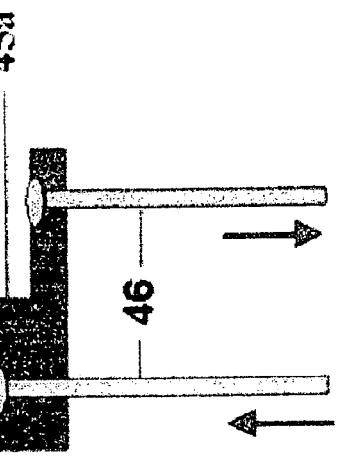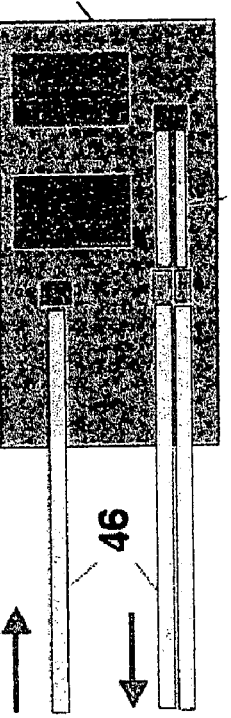
Figure 8A
44 Keyed optical ATR sensor tip
45 Keyed fiber optic fixture with integrated focusing optics
Figure 8B
47 Keyed optical transmission, turbidity or fluorescence sensor tip
48 Remote electronics module (within sensor) with optical fiber coupling
Figure 8C
49 Remote electronics module (within sensor) with optical fiber coupling and multi-wavelength sensing (two shown)

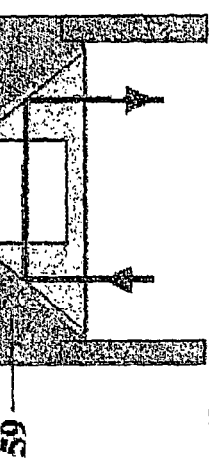
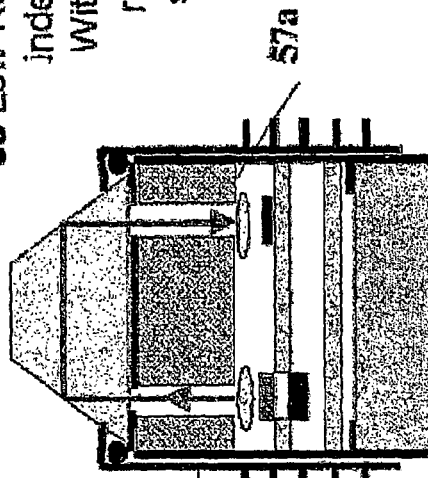
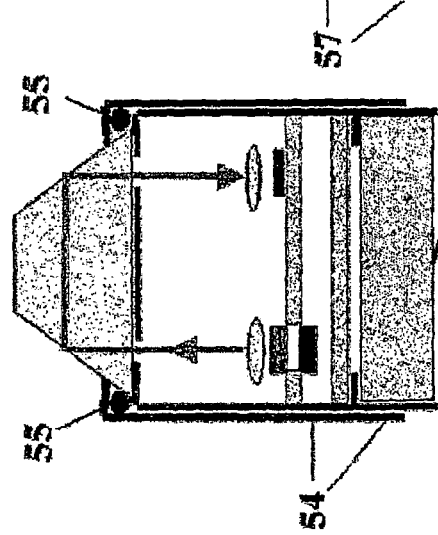
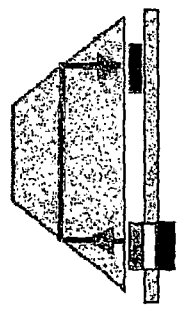
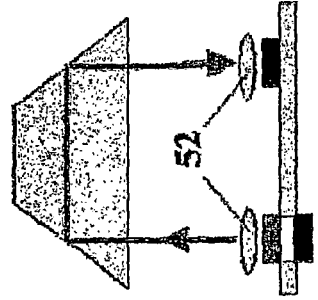

LOW-COST ON-LINE AND IN-LINE SPECTRAL SENSORS BASED ON SOLID-STATE SOURCE AND DETECTORS COMBINATIONS FOR MONITORING LUBRICANTS AND FUNCTIONAL FLUIDS

This application, filed under 35 U.S.C. §371, claims priority from International Patent Application PCT/US02/32621 filed on Oct. 11, 2002 and published in English under PCT Article 21(2), which in turn claims priority from U.S. Provisional Patent application Ser. No. 60/328,885 filed on Oct. 11, 2001.

FIELD OF THE INVENTION

This invention relates to optical sensors and associated systems. More particularly, it relates to such optical sensors and systems that may be used, for example, for the analysis and characterization of lubricants and functional fluids as used in the heavy equipment, automotive and transportation industries

BACKGROUND OF THE INVENTION

The role of optical spectral measurements for the monitoring of static and dynamic fluid systems is well established in the field of spectroscopy. Traditional systems involve the use of a spectrometric measurement system optically interfaced to a fluid stream. The standard format for such systems is some form of spectrometer or photometer (scanning) with some form of integrated sample handling system. In the case of spectrometer systems, commercial dispersive near-infrared (NIR) or FTIR (near- and mid-IR) instruments featuring some form of flow cell are good examples. Flow cells come in various forms for these types of applications, and can be used in transmission, transflectance (a combination of transmittance and reflectance) and internal reflectance formats. The internal reflectance format is often favored for traditional infrared measurements because it can be made to be minimally invasive and does not require a fixed film (fluid) thickness or optical pathlength. The latter can be constraining owing to the short pathlengths used in the mid-infrared region within a flowing fluid system. Furthermore, internal reflection probes are single sided and are easily inserted into either a flowing or static fluid system with no significant disruption to the fluid or the system being measured Examples of internal reflection probes are illustrated in U.S. Pat. No. 5,548,393 to Nozawa et al.

Optical spectroscopy, typically, but not exclusively, in the form of infrared spectroscopy is a recognized technique for the analysis and characterization of lubricants and functional fluids as used in the in the heavy equipment, automotive and transportation industries. Such spectroscopic measurements can provide meaningful data about the condition of the fluid and the fluid system during service. In the case of infrared spectroscopy, properties such as oxidation, coolant contamination, fuel dilution, soot, content, etc. can be derived by extraction of data from the spectrum. In most cases, this information is derived directly as a measure of the chemical functionality, as defined by the characteristic vibrational group frequencies observed in the infrared spectrum. Soot is a unique entity and is determined by a physical characteristic linked to light scattering and total light absorption (the nature of carbon particles).

While scanning systems are widely used for complex fluid systems, simpler, fixed wavelength, typically filter-based optical systems, are widely used for simple measurements on single-component and/or low-complexity fluid systems. For very simple systems, a single wavelength may be employed, thereby involving a very simple optical system comprising a source; often a polychromatic source used within a system that is optically constrained to a single measurement wavelength (frequency) by a suitable optical filter selected for the specific measurement. Such systems are used for the measurement of the following:
 a) a single chemical entity (if a unique absorption, emission or fluorescence can be identified),
 b) a phenomenon that involves optical attenuation, such as broadband absorption, turbidity or light scattering,
 c) or in the case of calorimetric measurements, the measurement of a single color entity.

More complex systems may be accommodated, and these require an increasing degree of optical complexity in terms of the ability to include additional analytical wavelengths to the measurement.

Traditionally, monitoring instruments are relatively large and expensive. If a simple, single-functional measurement is required it is possible to scale the device down in size. In essence, such a system involves only a light or energy source, a means for wavelength or energy selection, a means for interfacing with the sample and a means of detection. Such simple spectrometric/photometric systems can be made relatively small and compact.

Another factor to consider, however, is the operating environment. If a monitoring system is to be used in a relatively benign environment, such as in a laboratory or an ambient or conditioned indoor facility, then a traditional format of instrument may be used. If there is the requirement to measure a fluid system in a less conducive environment, such as on a process line (indoors or outdoors) or even on a vehicle or a mobile piece of equipment, then it is necessary to consider a system more ruggedly constructed than a traditional instrument. Standard enclosures are available that provide protection for instrumentation and these are commonly used for process monitoring applications. Such enclosures can include temperature and/or climate control and methods for vibration isolation.

The approach described above for transforming instrumentation into a format that is suitably prepared for monitoring fluids in "alien" environments (for traditional instrumentation) are expensive to fabricate. Furthermore, size can be a factor . . . once suitably packaged; even the simplest of measurement systems can become unnecessarily bulky or sometimes too large for convenient implementation. One option is to scale down the technology to the point where it becomes functionally equivalent to a sensor. For spectral measurement systems this is feasible. Examples exist for infrared measurements where combinations of microsources, optical filtration and small format detectors are combined to provide a practical monitoring system. The main problem with such devices is temperature sensitivity of the components and fragility in terms of long-term exposure to continuous vibrations. Also, intrinsically, like instruments, these devices are relatively expensive to fabricate.

SUMMARY OF THE INVENTION

The infrared spectral region is definitive in terms of the measurement of materials as chemical entities. However, the measurement can be difficult to implement in terms of the materials used. By their nature, the optics and associated materials are relatively expensive and do not lend themselves to easy replication and the production of inexpensive optical devices. For this reason, it is appropriate to consider the role of alternative spectral regions. The absorption of carbon (as encountered in diesel engine oil soot) extends into both the NIR (near-infrared) and visible spectral regions. Fabrication materials in these spectral regions are much less expensive and are amenable to easy replication by simple molding techniques, etc. An example here is that materials such as glasses or plastics, which may be cast inexpensively in a mold, and can be used as optical elements in this region of the spectrum. Furthermore, solid-state devices, such as LEDs (light emitting diodes) and silicon-based detectors (such as photodiodes), which are rugged, easy to implement electronically, and inexpensive, can be used in these spectral regions.

The concept of internal reflection, referenced earlier, can be applied in any spectral region. The only important requirement in the case of the measurement of the carbon absorption of soot is that the refractive index of the refractive optics used for the internal reflectance measurement be greater than the refractive index of the fluid matrix under study. Ideal materials should have indexes of refraction in the range 1.50 to 2.20. High index glasses, such as high lead glasses, fall into this category, also certain high index plastics. The benefit of such materials is that they can be obtained relatively inexpensively and can be shaped via molding processes. Different configurations of solid-state source-detector pairs combined with different refractive glass or plastic components, can provide for internal reflectance, light scattering, and transmittance measurements of oils and related fluids. In the spectral region of interest, neither glasses nor plastics have any significant spectral absorption and hence do not constitute any form of optical interference on the measurements.

Taking into account the factors of size, thermal stability, vibration immunity and cost (with an implied ability to mass-manufacture) a new fluid measurement system is described. This system includes the use of solid-state light emitters, low-cost, solid state detectors, integrated with opto-electronics that remove, or compensate for, any temperature dependency effects, low-cost optics that may be mass-produced by molding techniques (if required), and low-cost packaging that may also take benefit from molding methods. The optical interfacing is accomplished with a simple refracting element that can be configured to provide both internal reflectance and transmission modes of measurement, as well as light scattering or fluorescence as secondary measurements. The solid-state light emitters provide the monochromatic light source required for the spectral measurement, and may be used in multiples where more than one analyte or spectral measurement is to be made. In the latter case, techniques such as output modulation can be used to differentiate the individual sources of energy/light. The use of multiple wavelengths provides additional flexibility and performance for oil condition measurements, and accommodates the complexity of the oil degradation processes; providing possibility of linearization of otherwise non-linear measurements.

Because of the lack of availability of low-cost mid-infrared sources and detectors, the focus of the preferred embodiments of the invention is on monitoring devices that operate in the visible and near infrared (typically, but not exclusively, <1100 nm). However, the invention is not limited exclusively to these optical ranges, and the application to the near-infrared and mid-infrared (out to 25,000 nm/25 µm) is included in the event that cost-effective mid-infrared monochromatic sources and suitable low-cost detectors become available (currently these devices are cost-prohibitive). The range currently specified has been linked to the use of glass or glass-like materials (for example fused silica) or plastics for the optical interfacing and the use of low-cost silicon photodiode detectors (range limited to <1100 nm).

The sensor devices described in relation to this invention are for use as monitoring devices for lubricants and functional fluids in automotive vehicles, heavy equipment, and various forms of transportation that involve dynamic fluid lubricant and power conversion systems. They include sensor devices for monitoring engine oils, transmission oils, hydraulic oils and fluids, turbine oils, coolants and any fluid system that protects mechanical moving parts or transmits power to moving parts. A specific sensor device may be located within a moving stream, or at a point in the lubrication or fluid transfer system where there is a sufficiently frequent refreshment of the analyzing surface during the period of measurement. The period of measurement can be extended from a few minutes to a few days for systems where the change in lubricant or fluid composition (chemistry) changes slowly.

The following discussion relates to the use of the sensor devices on a vehicle, as this serves as an appropriate example. However, the devices are, as indicated, intended for use in all forms of lubrication system. In the case of a combustion engine, as in a heavy-duty diesel vehicle, it is expected that the sensor will be mounted in the filter block, on the output side of the filter (as illustrated in FIG. 1) or in the flow line to or from a secondary filtration system, such as a bypass filter. This location provides a filtered refresh stream, which is on the return to the engine, and hence is on the cool side of the engine lubrication system. Although the sensor is intended for operation at elevated temperatures, attempts should always be made to locate the devices in the coolest regions, thereby reducing the incidence of thermal stressing. In the case of the transmission, the sensor may be mounted either in a filter zone (if one exists), in an external oil cooler (if one exists), or at a point internally within the transmission (as noted in FIG. 1). Other potential locations on a vehicle for the proposed spectral sensor devices may include the coolant system and the hydraulics (such as the braking system).

The sensor is preferably a low voltage device having a minimum power requirement. The device may be made available with various electronics packages, from a simple digital output device to a smart sensor that provides processed numerical data. The output from the sensor can either go directly to a display, such as a simple status light, for example, a three state LED: green (OK), yellow (warning) and red (alert or problem); or to an alpha-numeric or a graphical display (for example, an LCD display). Alternatively, the sensor can provide a standard format output to a vehicle or equipment data bus, supplying diagnostic data to an on-board computer, which in turn supports an intelligent sensor output display (see FIG. 2).

The individual sensors may include an integrated module comprising one or more sources of electromagnetic radiation, in the form of solid-state emitters and one or more solid-state detectors. Sensors may also includes a single component optical interface fabricated as a refractive optic, working in an internal reflectance or optional transmittance modes (or light scattering or fluorescence modes), and integrated electronics that include circuits that provide optical compensation, temperature sensing and compensation, analog and digital signal processing, and external communications. The system is designed to allow a high level of integration of both electronic and optical components, and to include packaging that provides both thermal isolation (if required) and ease of assembly and manufacture. Fiber optics or other forms of optical light guide or light conduit may be used, with appropriate source collimation and detector collection optical elements. Examples of fully fabricated sensing devices are provided (in FIG. 9). The sensor tips and the associated optical interfaces/electronics module are designed for interchangeability with built-in self-alignment (FIG. 8). This provides a range of sensors and sensor options with a common architecture for internal reflection, optical transmission, turbidity and fluorescence measurements. A sensor system is thereby formed that can be readily adapted for a wide range of sensing measurements; from soot monitoring in diesel engine oils to lubricant aging and degradation in transmissions.

The optical principles used for the measurements are internal reflectance, transmittance, fluorescence and light scattering, dependent on the specific physical or chemical functionality to be measured. The sensor tips can be further functionalized by the chemical and/or physical modification to the detection surface(s). This provides the option for monitoring of specific chemical functionalities by light transmission or fluorescence measurements. Additionally, surface coatings may be applied to the optical surfaces to enhance surface protection (if required) and or reduce fouling. FIG. 6 provides example configurations for these modes of measurement. Based on current technology and material availability, the measurements cover the visible and near-infrared spectral regions. It should be noted that there are cost benefits to limiting the system to the shortwave NIR (to 1100 nm); low cost photodiodes and plastic lenses and fiber optics may be used. The principles of this invention can also be extended to longer wavelength regions, which may include the traditional infrared in the event that suitable materials and components become available that conform to the basic requirements of ease of manufacture and fabrication, and low-cost.

Where practical, both optical and packaging components may be mass-produced by techniques that allow for low cost fabrication, including molding, sintering and/or extrusion-based processes. This includes the use of mold-conformable materials such as glasses, composites, resins and plastics/polymers.

BRIEF DESCRIPTION OF THE DRAWINGS

FIGS. 3A through 3H are side elevational views of conical sensor probes in an internal reflectance configuration, in accordance with the invention.

FIGS. 3I through 3K are bottom plan views of the sensor probes of FIGS. 3F through 3H respectively.

FIGS. 5A and 5B are cross sectional views of sensor probes in accordance with the invention in transmittance configurations.

FIG. 5C is a top plan view of the sensor probe of FIG. 5A.

FIGS. 5D and 5E are top plan views of sensor probes in accordance with FIG. 5B.

FIG. 5F is a side view of the sensor probe embodiments of FIGS. 5A, and 5C to 5E, showing that these sensor probes use a conical reflection surface.

FIG. 5G is a top plan view of the sensor probe of FIG. 5A, configured with facets as reflecting surfaces.

FIGS. 5H and 5I are top plan views of sensor probes in accordance with FIG. 5B, configured with facets as reflecting surfaces.

FIG. 5J is a side view of the sensor probe embodiments of FIGS. 5B, and 5G to 5I, showing that these sensor probes use facets as reflecting surfaces.

FIGS. 6A through 6E are cross sectional views of conical sensor probes, in accordance with the invention, in various spectral measurement modes.

FIGS. 8A to 8C illustrate various sensor probes with fiber optic coupling and remote electronics packaging options, in accordance with the invention.

FIG. 9A to 9E illustrate various integration and packaging options for conical sensor probes in accordance with the invention.

DETAILED DESCRIPTION OF TIRE PREFERRED EMBODIMENTS

Figure 1A:
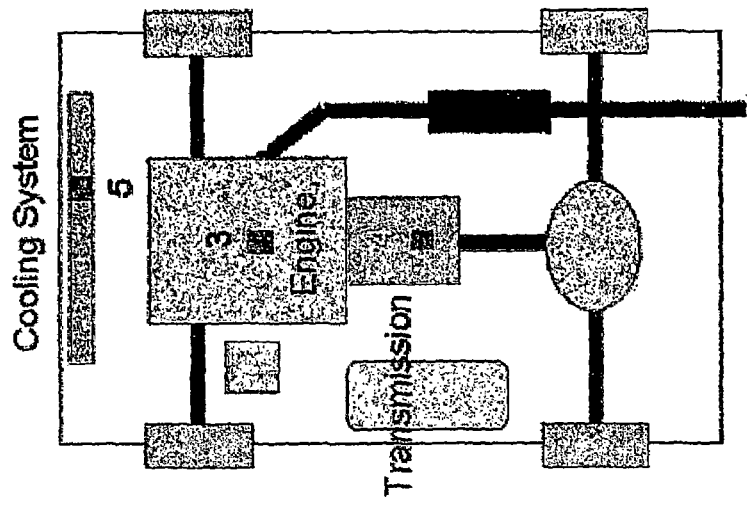
FIG. 1A is a schematic plan view of a vehicle, illustrating locations for functional fluid sensing devices in accordance with the invention.
Figure 1C:
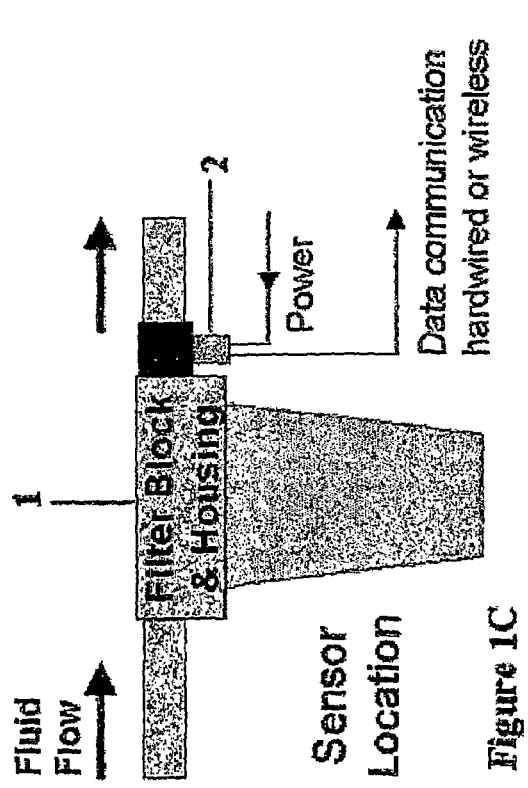
FIG. 1C illustrates an engine oil condition sensing device in accordance with the invention mounted on the oil return line from the oil filter to the engine.
Figure 1B:
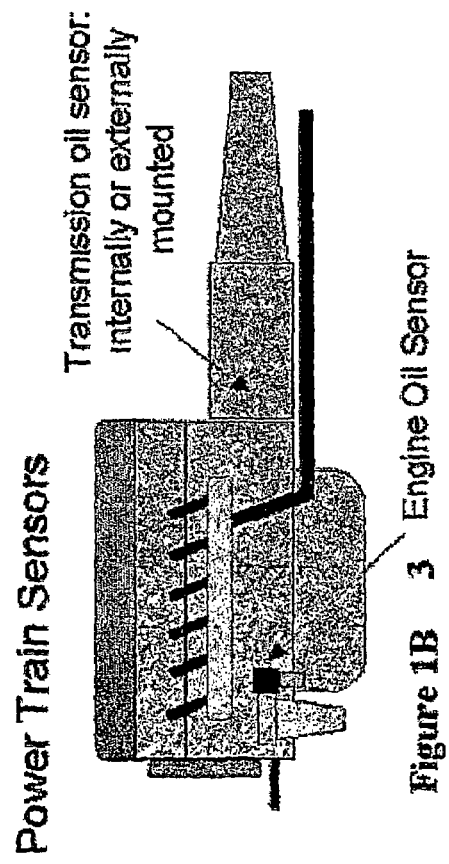
FIG. 1B illustrates an engine oil condition sensor mounted on an engine.

The system will now be described in terms of the main functional components:

The implementation of the sensor in automotive and heavy equipment applications is signified in FIGS. 1A to 1C. Prime applications for the sensor are for soot level monitoring in heavy-duty diesel engines and oil condition monitoring (oxidation and nitration) in gasoline and natural gas-fired engines. In both cases, a good location for the sensing device (2) is at the output side of the engine's primary (or secondary) filtration system, where the sensor is inserted into the stream on the return side of the filter-housing block (1). The device, as indicated will receive low-level power, which is either provided by a data bus or via the normal power distribution system of the vehicle. The output from the sensor, in some form of data communications, is fed back to a display, a data bus, or an on-board computer system. The advantages of mounting the sensor on the filter block (3) are that the access is convenient, it is externally mounted, and it is in one of the cooler regions of the engine. Alternative positions for the sensor can include the transmission (4) and the coolant system (5).

Figure 2A:
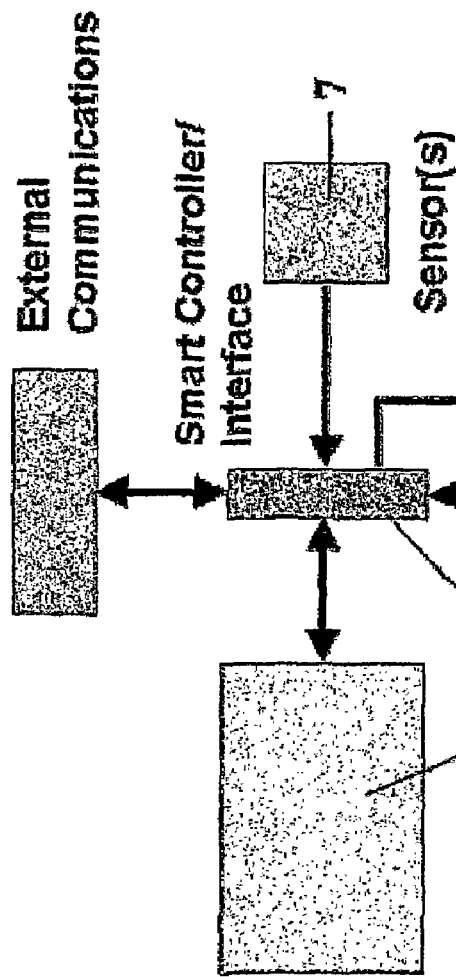
FIG. 2A is a block diagram illustrating the integration of a device in accordance with the invention with an existing vehicle system.
Figure 2B:
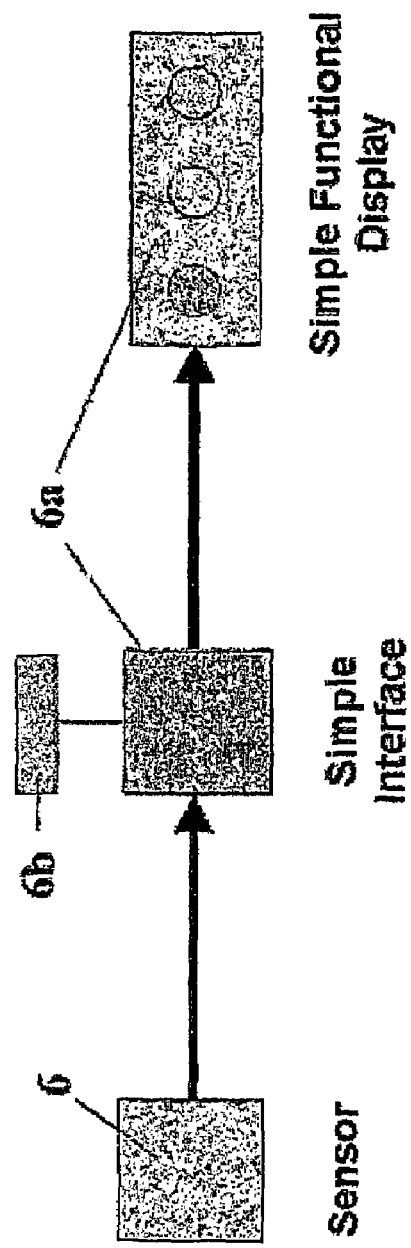
FIG. 2B is a block diagram of a dashboard based fluid condition indicating system, which may use a sensor in accordance with the invention.

Referring to FIGS. 2A and 2B, with one or more of the optical sensors on board a vehicle, there is the need to provide the results back to some form of a display or on-board data handling system. Most heavy-duty vehicles already have a significant number of sensor systems in place (but not fluid condition sensors), and these communicate back to the operator/driver via alarms, alerts, displays or status lights. In some cases these are activated by direct connections with the sensor (6), other times it is via a vehicle management system (7a), involving an on-board computer and data manager. In the case of the spectral sensor for soot content and oil condition, it depends on how the device is implemented. If the device is installed at the time of manufacture of the vehicle or the engine then it is probably more expedient to couple the system into a vehicle management system (7a). If it is installed as part of the after market (at a service center or an vehicle parts store) then the direct connection route to a simple status display on the dashboard is a more practical implementation.

Regardless of the form of installation, in accordance with the invention, the life of the light emitting element, usually a light emitting diode, as more fully explained below, may be extended, by pulsing only when measurements need to be made. This is especially advantageous at high temperatures, such as those encountered under the hood of a vehicle having an internal combustion engine, where the output of a light emitting diode is not affected as much by the presence of higher temperatures, as by operating at such higher temperatures. This function may be implemented with an emitter pulsing circuit (7b) in FIG. 2A and (6b) in FIG. 2B. An optional temperature sensor (not shown) may be provided in close proximity to the respective sensors (7) and (6), to sense the local temperature, thus providing the ability for intelligent power management whereby the LED is only powered in an operational temperature range that maintains the lifetime of the device output. If the source has to be powered at higher temperatures the device will be modulated in short bursts to minimize the instantaneous power on the LED while operating at elevated temperatures.

The Optical Imaging System

Reference is now made to FIGS. 3 to 7. The main optical components are based on a cone structure, with or without the apex (FIG. 3), and with or without side facets (items 12 and 13 in FIGS. 3G, 3H, 3J and 3K). In the configurations shown in FIG. 3, the optical imaging system is functioning as an internal reflection device as designated by the beam paths 14. This mode of operation is intended for measurements of the light (or energy) absorption of highly opaque, dark or strongly colored media, such as the soot content of used diesel oil. As shown, the system functions as a two-reflection system. The inclusion of facets in the side of the conical structure (12 and 13) is intended to provide more precise directional imaging for the reflected beams. In one illustrated example, three independent, internally reflected, optical beams can be handled with this six faceted system. Note that the number of facets can be from two to possibly as high as eight or ten. The only limitations are the size available for the sensor, and the internal dimensions of the electronics. Generally, six or eight is a reasonable number.

Figure 4A:
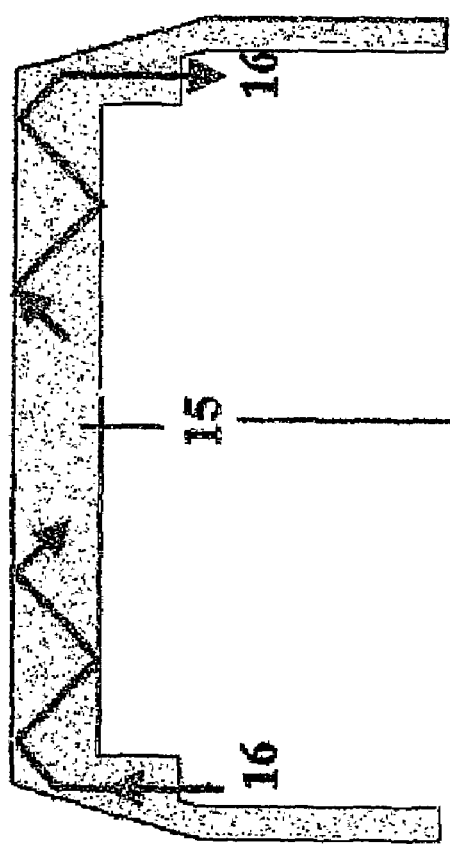
FIG. 4A is a cross sectional view of a conical sensor probe in accordance with the invention having an extended internal reflectance configuration.

The two-reflection system works well for the heavily loaded and highly opaque samples. In the event that lower levels of the absorbing material require measurement it may be necessary to extend the number of reflections through the internally reflecting imaging system. This is achieved by establishing a multiple internal reflection systems as shown in FIG. 4A. The approach shown in FIG. 4A is the well-established optical technique known as multiple internal reflection or evanescent wave measurement. An example of a possible imaging system element is shown in FIGS. 4A and 4B, in the form of a molded enclosure with the sampling face in the top part of the cone.

The alternative cone structures shown in FIGS. 3A and 3D (8a and 10a) accommodate an increased number of reflections, providing 4 and 3-reflection optics, respectively. However, these structures are also intended to accommodate lower index of refraction optical materials, allowing the use of lower-cost glasses or plastics. The base structure (10), that features two reflections, is used throughout for illustrations of implementation for simplicity. This structure features a nominal 45° base cone angle, and is intended for glasses, and other optical materials with indexes of refraction of 2.0 or greater. The alternate half-cone structure (10a) has a 60° (or greater) base cone angle and is intended for glasses, or other transparent materials, with lower indexes of refraction, possibly down to 1.5 dependent on the critical angle for the measurement. The third structure, which features a double apex cone (8a), which is shaped to provide four reflections, is intended for glasses, or other transparent materials, with indexes of refraction between 1.70 and below. These values are based on a nominal index of refraction for the lubricant or functional fluid in the range of 1.35 to 1.50, with an average value expected to be between 1.42 and 1.46.

Note that the structures described show the internal reflections occurring at the internal curved surfaces of the cone. Dependent on the fore imaging and the post imaging of the optical structure, this may result in light losses, which may interfere with some measurements. In such cases, alternative structures that feature flat reflection surfaces, as facets in the structures surface will provide the identical internal path. In the case of the 2- and 3-reflection structures (10 and 10a) the facets can also be placed in a simple cylindrical cross-section optical component, as indicated (10b). In all cases, irrespective of the shape of the original structure—cone or cylinder—the facet is cut to the required angle of 45° for the two-reflection structure and 60° (or greater) for the three-reflection structure. The multi-faceted structure (13), which is intended to accommodate typically between 2 and 4 reflection paths (4 to 8 facets), can also be fabricated, if required, on a cylindrical base structure (9), dependent on whether the facets are cut or molded.

Figure 4B:
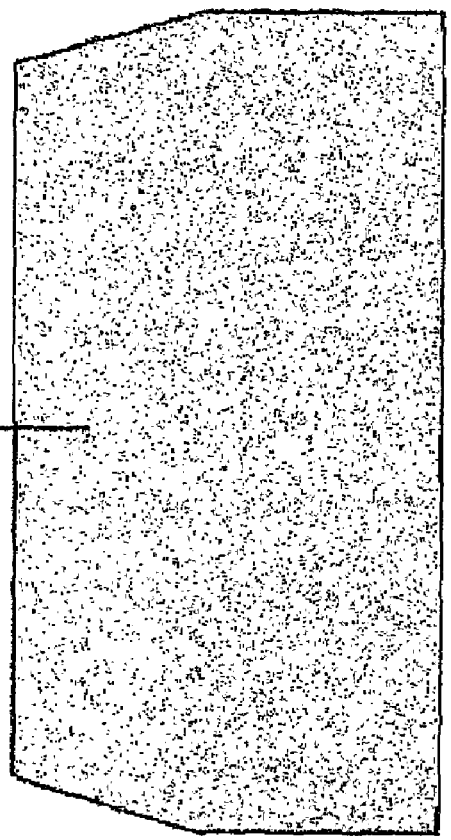
FIG. 4B is a side elevational view of the sensor probe of FIG. 4A.

The component shown in FIGS. 4A and 4B is considered to be a shallow cone, where the view shown is the side cross-sectional view. The main component will be circular in construction when viewed from the top. The reflection path shown (16) is only one example of internal reflection through such an optical element. Other configurations can be considered by changing the side angle of the cone. This structure is designed to fit into a similar structure as a single-ended sensor probe, as the components shown in FIG. 3. It is envisaged that a molding process will used to form this type of structure.

The following governing expression is useful in deciding the performance of the optical structure in terms of measurement sensitivity:

$$D_p = \lambda / (2\pi n_1 (\sin^2\theta - n_{21}^2)^{1/2})*$$

*Book reference: Coates, J. P. "The Industrial Applications of Infrared Internal Reflectance Spectroscopy", "Internal Reflection Spectroscopy: Theory and Applications", Ed. Francis M. Mirabella, Marcel Dekker Inc., 1992.

Where: $d_p$=depth of penetration of the light/energy into the fluid medium
$\lambda$=measurement wavelength (nm or μm)
$\theta$=angle of incidence (defined by the cone or facet angle)
$n_1$=index of refraction for the refracting element/optical structure
$n_2$=index of refraction for the sample/fluid medium/lubricant
$n^2_2=(n_2/n_1)^2$ The depth of penetration, defined in terms of the wavelength units (typically nm or μm) is an important term because it can be used to tune the sensor to the measurement. It can be used to define both the dynamic range of the measurement and the sensitivity of the measurement. In the design of the sensor, there are two parameters that can be modified and adjusted to provide different degrees of sensitivity for the measurement: the angle (θ), which is defined either by the cone or the facet cut angle, or the refractive index of the material (glass or plastic) used for fabrication. One of the advantages of using a glass is that the formulation (recipe) of the glass can be adjusted to provide a desired final index of refraction. Also, with the use of facets, each facet-pair can be cut to provide different angles of incidence (θ). In this latter case, by the use of two or more facet-pairs, a single sensor can be tuned to provide two different measurement ranges. In this type of fabrication, a practical approach is to cut the facets into a glass rod structure with a flat top.

The optical sensor is intended to be extended to the measurement of fluid systems that will require longer pathlengths than can be generated by the internal reflectance mode of operation. FIGS. 5A to 5J are, by way of example, embodiments of the manner in which the internal reflection element can be modified to handle transmission, and related extended path measurements. An alternative set of optical imaging elements are included to provide a means of measuring optical transmission through a range of different media These configurations can also be used to monitor light attenuation as the result of turbidity and/or light scattering. Adaptations of the conical structures previously shown in FIGS. 3A to 3K include a measurement channel or cavity where the liquid can enter and can be measured at a predefined pathlength (or pathlengths) as shown in FIGS. 5A to 5J. Two simple examples are shown that provide a slotted channel for higher absorbances, and an open channel for longer pathlength measurements.

The open channel unit also lends itself to light scattering measurements (FIG. 6D). The light scattering measurement can be considered when low levels of particulates or low levels of turbidity (such as caused by moisture contamination) have to be detected in the latter case, it can be the measurement of a specific marker or fluorescent impurity of contaminant. This class of sensor opens up the opportunity of utilizing specific markers for quality assurance and/or specific types of contamination (as in the aviation industry . . . engine oil contaminating hydraulic oil, and vice versa).

The need to provide low-cost components has driven the choice of fabrication materials. The selection of the visible to the shortwave near-infrared spectral region enables the use of glass, plastics or related materials instead of the more sophisticated and more expensive optical elements used in the traditional infrared spectral region. The use of the internal reflectance mode, both for the internal reflectance measurement, and for the optical interfacing used for the other modes of measurement require the use of a high refractive index material. As previously noted, the target range is in the area 1.50 to 2.2 for the index of refraction, and commercial high index glasses, such as SF4 (1.75), SF11 (1.78), SF6 (1.81), SF57 (1.85), SF58 (1.92), SF59 (1.95), and LASF35 (2.02) supplied by Schott Glass, serve as appropriate examples. Schott supplies these as high optical quality glasses. This quality is not required for the application disclosed, and lower grades of comparable composition materials can be used for volume production.

In the form described above, the long pathlength versions of the spectral sensor require the imaging optic, within the main optical structure, to be fabricated from a high refractive index material (typically a RI >2.0). This may restrict the choice of materials. In an alternative embodiment of the sensor head (50), shown in FIGS. 9A to 9E, a version featuring low-refractive index glass is presented. In this version, the reflection occurs at a reflective surface, which may be an aluminized back surface, or a reflective film, such as a metal foil film. In this configuration, the optical structure and reflective film are protected from the environment by a close fitting shroud, providing a nominal cylindrical cross-section, as illustrated in FIG. 9E (59). An example of fabrication here is that the shroud be molded from a plastic or similar material, and that the glass or plastic optical structure and the associated reflective film surface (60) be either molded or bonded in place forming a single sensor head entity that can be coupled to the remaining opto-electronics of the device, as indicated in FIG. 9E (58). This sensor format may be used for all transmission and light scattering modes described earlier.

The Opto-Electronic Components

Two key components that form the basis of the solid-state spectral measurement system, are the LEDs (light emitting diodes), that are used a spectrally selective sources and the silicon detectors. Silicon photodiode detectors have the advantages of high sensitivity over a broad spectral region (nominally 400 nm to 1100 nm), linearity, robustness, and availability in a large number of packaging options, and at extremely low cost (a few cents). There are other forms of solid-state light detector, and these are also included here for consideration, if warranted by a specific application. In cases where cost is an issue these may not be an option.

LEDs offer the advantages of color or wavelength specificity, constant output, low power consumption, no significant thermal output, the device output can be modulated at unique frequencies, compactness and robustness, availability in a large number of packaging options, and extremely low cost. A relatively wide range of spectral wavelengths are available from LED sources, and some common examples are included Table 1.

TABLE 1

Example Wavelengths Available from LED Sources

| Color | Wavelength |
| --- | --- |
| Blue | 430 nm |
| Green | 555 nm |
| Yellow | 590 nm |
| Yellow | 595 nm |
| Orange | 610 nm |
| Orange | 620 nm |
| Red | 625 nm |
| Red | 660 nm |
| Red | 700 nm |
| Sw-NIR | 880 nm |
| Sw-NIR | 940 nm |

Certain of these LEDs are available with matching detectors, examples being the short-wave NIR LEDs, which are commonly used for remote "infrared" monitoring and control —a practical example being a TV remote control. Another benefit provided by certain LEDs is the ability to operate at two or more states producing more than one wavelength (such as red, yellow and green) from a single device. This enables a very compact design using a single source and single detector, and where the output for individual wavelengths is differentiated by sequence or by different modulation frequencies. In certain measurement systems up to four or five unique wavelengths (for example: blue, green, yellow, red and NIR wavelengths) will be monitored, each as individual wavelengths, each detected by a single (or multiple) detector, and differentiated based on sequence or modulation frequency. The multiple channels will be modeled to provide color profiling and multiple component determinations.

In its final form, the sensor is comprised of one or more LEDs, individually modulated, and coupled to an optical feedback system for monitoring the outputs of the LEDs, independent of the sampling channel. This system is incorporated to compensate for drift in the output of the LEDs as a function of temperature and degradation over time. The feedback detector would be located in close proximity to the system detector (prior to the optical interface) to model the response changes of the detector system. This arrangement makes the system virtually immune to drift and fluctuations as a function of temperature. Also, the use of the second detector provides a reference independent of sample absorption, and as such can provide a direct ratio $I_0/I$ which is used to calculate the effective absorption (proportional to species concentration): absorption=−log $(I_0/I)$, where $I_0$ is the reference intensity, and I is the intensity after the sample absorption. The optical and electronics system can be a single integrated circuit board or device, possibly featuring (but not explicitly) application specific integrated circuits (ASICs) for the signal handling, computations and data communications. This integrated opto-electronic component may be encapsulated, and should include some imaging optics, accomplished by some form of molded optics in front of the source(s) and detector(s).

Figure 7C:
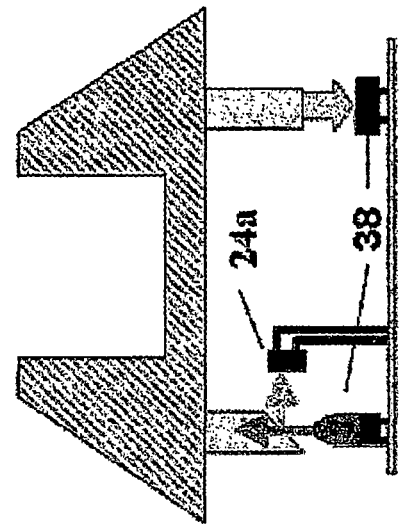
FIGS. 7A to 7F illustrate various solid-state source (illuminator)/detector combinations, in accordance with the invention.
Figure 7B:
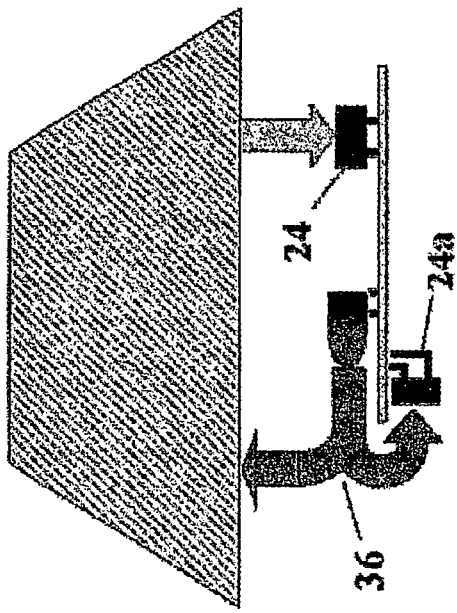

The placement of the opto-electronic elements—the LEDs and detectors—will be important to ensure optimum imaging through the optical interfacing structure. This is a simple process once the electronics and opto-electronics are mass-produced. In a standard environment, with moderate operating temperatures, the opto-electronics is close-coupled to the optical interfacing structure. Typical distances maybe from about 1 mm to 2 cm. At the shorter distances, no additional imaging optics is contemplated (FIG. 9A, 50) but this is not necessarily the configuration of choice. At the longer distance (FIG. 9, 51), supplemental lenses (FIG. 9B, 52), made from glass or plastic, in front of the LED source(s) and detector(s) are used to improve image quality. Alternatives will include the use of light conduit, from the optical interfacing structure to the opto-electronics—both source(s) and detector(s). Light conduit can be in the form of glass rod (index matched or otherwise), hollow light guides or optical fibers. One situation featuring fiber coupling of the source is indicated in FIG. 7B (36). Note that in applications that involve high temperatures (80° C. or higher), such as close coupling to an engine, the option to use an insulating material between the optical interface structure and the opto-electronics is important (FIG. 9D).

The Packaging

Examples of options for integration and packaging are presented in FIGS. 9A to 9E. The packaging enclosures are intended to be fabricated from low-cost materials (FIG. 9C and 9D, 54, 57 and 57a). Examples can include aluminum moldings or extrusions, machined plastics, and plastic moldings, castings and extrusions. The selection of material will be based on the requirements of the application and cost. In cases where high temperature applications are involved (80° C. or higher), a provision for providing external cooling fins (FIG. 9D, 61) and the use of thermally insulating materials 62 between the optical structure and the opto-electronics are provided as options in the design.

Two fundamental designs may be used for the monitoring of lubricants and functional fluids. One design takes advantage of the optical phenomenon known as internal reflectance, or evanescent wave spectroscopy. This is intended for the measurement of optically dense media, and in particular for media that exhibit high levels of light absorption. This is particularly the case for the measurement of the soot content of heavy-duty diesel engine oils. In this case, dependent on the engine type and usage, the soot content can be elevated to levels of 5% or greater, possibly as high as 8% or 9%. At high levels, the oil is progressively thickened, it becomes potentially abrasive, and it places stress on the dispersant additive package of the lubricant. In all cases, the soot, which exists as finely dispersed carbon particles, is maintained as a stable suspension in the lubricant by the additive package. Soot is a universal absorber of visible, near infrared, and infrared radiation. At high levels it is impossible for the light/energy to penetrate. In order to obtain a meaningful measurement of the light/energy attenuation by the carbon, one resorts to an internal reflection method of measurement.

Referring again to FIGS. 3A to 3K, five different structures are illustrated (8a, 8, 9, 10 and 10a) for a simple insertion-style sensor probe. These are nominally conical in shape, with a circular cross-sectional base. A circular cross-sectional base (11), for example, in a rod or cylinder-form (9), is preferred in terms of providing a good environmental seal when the optical structure is mounted into the main body of the sensor probe. The cross-section design of the probe is dependent on the intended methods of fabrication and on the intended light path. The light path (14) has an angular dependency, and this is dictated by the critical angle of the sensor tip; critical angle in this case is the relationship between the index of refraction of the fluid medium and the material used for the sensor tip. If low index materials are used for construction (such as <1.50), a structure that provides up to 4-reflections (with high reflection angles) may be preferred to ensure correct optical performance (8a). At the opposite end of the scale, a simple 2-reflection system (8 and 10), with a 45° cone or half-cone, is recommended for high index materials (>2.0). In the mid-range, with indexes of refraction >1.5 and 2.0, a 60° half-cone configuration is proposed (10a), providing a total of three internal reflections. Note that this configuration is not restricted to a 60° angle, and other angles may be used between the facets or conical surfaces.

The internal reflections of the configurations described (8, 8a, 9, 10 and 10a) occur at curved surfaces in the case of a pure conical structure. Dependent of the nature of the source and detector, there is a potential to lose optical efficiency via defocusing of the beam. An alternative set of configurations involves forming the surfaces, either on cone or cylindrical optical structures (10b), as facets with a flat reflecting surface. Such a surface may reduce the defocusing effect for certain configurations. The system proposed can utilize from two (1-channel) to eight (4-channel) sets of facets providing from one (13) to four separate beam paths respectively. An example accommodating three separate beam paths is also illustrated (13) with six facets.

FIG. 4A illustrates the use of multiple reflections, beyond those accommodated by the cone structures discussed so far (FIGS. 3A to 3K, 8a and 10a). In FIG. 4A, there is the option to provide multiple internal reflections over an extended area by the use of a more conventional internal reflectance configuration (15). In this case the beam path includes multiple reflections that are defined by the angle of incidence of the beam (16), the diameter of the cone (cross-sectional length) and the thickness or effective height of the shallow part of the cone (the opposing faces that provide multiple internal reflections). This type of structure, which is formed as a molded part can be used in the standard mounting regime. This structure is only recommended in the event that an effective molding procedure is available.

Reference is made to FIGS. 5A to 5J. The standard 45° wedge structure described for internal reflectance measurements can also be adapted for other optical measurement modes, including transmission, fluorescence and light scattering measurements. These involve the formation of an open path or channel in the structures 17 and 18 to allow the fluid to flow between a pair of optical surfaces that provide a transmission path for the optical beam (19 and 20). In the transmission mode the absorption measurement is proportional to the thickness or width of the channel path. This can be in the form of a narrow slot (19) for opaque or highly absorbing fluids, or as a wider cavity or channel 20 for lower absorption samples. In applications where more than one optical channel is used, or where more than one wavelength is used for a measurement, the open path area can be modified to handle differences in the absorption of the material at the different wavelengths (22, 23 and 23a). In cases where the optical dynamic range needs to accommodate different levels of the same material, the staggered light paths suggested for different wavelengths can be equally applied to a single wavelength (or sets of wavelengths), thereby providing the ability to acquire data from different levels/concentrations of the same material. This can be important for scattering media and turbidity measurements, especially if the medium can change from being completely transparent to partially opaque. The use of optical paths of different lengths through the material under test will also permit a greater dynamic range of measurement to be achieved.

As previously discussed, the structures can involve either natural internal reflections where the structure material has a sufficiently high index of refraction to sustain internal reflectance, or forced internal reflections, where a mirrored or metalized surface (21) is used to generate the reflections. The reflective coating or film can be protected by either the use of a protective shroud or enclosure (FIG. 9E, 59) or by the application of a suitable impervious film (such as an epoxy resin or similar chemically resistive surface) over the film or coating (21a). FIGS. 5C to 5F use the conical surface for reflection. In FIGS. 5G to 5J, facets are added and used as the reflecting surfaces.

In FIGS. 6A to 6E, the practical application of the sensor, the main optical structure and the opto-electronics are combined to provide for different measurement modes. The simple standard mode (FIG. 6A), featuring the internal reflectance probe head (25) can accommodate the 2, 3 and 4 reflection conical structures (Example: FIG. 3K, 13). The source(s)/LEDs (24) and detector(s) (24a) combination(s) are positioned to provide optimal coupling with the required light paths within the optical structures. The transmittance mode (FIGS. 6B, 6C, and 6D) is implemented in an essentially identical manner to the standard internal reflectance mode, with the clear aperture defined for short (19) or long (20) pathlength measurements. In this case, the two-reflection configuration must be used. In the event that a low refractive index element is used, reflective surfaces must implemented on the cone faces or on the facets (FIG. 9, 59). Typically, the reflective surface is expected to be either an aluminized coating or a thin metal foil (such as aluminum) coating. In both cases the metallized surface should be protected from the measurement fluid. A packaging option to provide the necessary protection is provided in FIG. 9 (59).

The open path structure option (FIG. 6D), especially with the large pathlength cavity or channel (20), is a suitable platform for simple light scattering and turbidity measurements. This configuration uses a secondary light path featuring an additional detector 32. This provides the option to measure light attenuation with the standard detector (24a) and the presence of scattered light (energy) with detector (32) placed under the second light path (31).

Reference is made to FIG. 6E. In this embodiment, the interacting material 21a or 28, in the form of a porous matrix, which may be a gel, an adsorbent or a membrane, or other adsorptive medium is placed in intimate contact with one or more of the measurement surfaces. A porous protective layer (29a) may be implemented to protect the interactive coating or membrane 28 from the environment. In the case that a protective layer is used, the material selected is expect to remain inert and have adequate porosity to allow ready interchange between the fluid medium and the interactive coating or membrane.

In the transmission mode of operation (FIG. 6C) the interactive layer (coating or membrane) may placed on both the entrance 29b and exit 29a of the measurement cavity. This format allows more than one type of measurement to be made. It should be noted that if the sensor is configured to handle multiple wavelengths that the interactive layer can contain a cocktail of immobilized reagents or reaction centers. This permits multiple component measurements to be made.

In the embodiments that feature internal reflection (26) for fluorescence measurements the structures are arranged to provide either natural internal reflectance, where the index of refraction of the main optical structure is sufficiently high to sustain internal reflection, or forced internal reflectance where the first reflection surface contains a reflective surface formed by a metallic coating or film (21 and 28). In the case of natural internal reflectance, the excitation beam is retained and returns to the detector. In this case, a rejection or blocking filter is required to prevent interference from the excitation wavelength. Alternatively, if a single fluorescence wavelength is to be monitored, a bandpass filter for that wavelength can be employed. In both instances the filter is placed in front of the detector (24a).

Figure 7A:
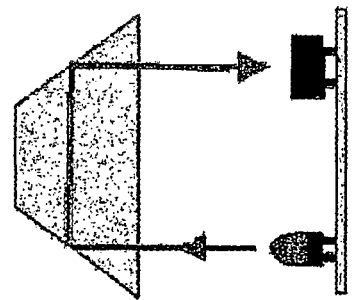

As illustrated in FIG. 7A, the source(s)/LED(s) and detector(s) combination(s) are mounted at positions optimal to the optical path of the main optical sensing structure on a common electronics board or device (35). It is expected that a given system will accommodate up to 4 source-detector pairs; possibly more dependent on optical layout and component size and output. If the system is to be operated at ambient temperature only, the output of the source, and the response of the detector are expected to be constant and reproducible. In most practical scenarios, the temperature is not expected to remain a constant during the measurement periods. Most solid-state detectors have some form of temperature dependent response. Also, the output of the LEDs can change with time and operating temperature. In order to accommodate this, a secondary detector system 24a is used to monitor both changes in source output with temperature, and to mimic the response characteristics of the main detector. Balancing electronics are incorporated to provide temperature compensation based on the output of the secondary detector, thereby providing a stable optical signal output at all temperatures. Three example configurations of the secondary detector (29, 29a and 31) are shown in FIGS. 7B and 7C, featuring a optical fiber split (36) and a light conduit split (39). In the case of the light conduit split (39), the conduit material may have the same or similar in index of refraction to the main optical structure. The light to the secondary detector is provided by front surface reflection from the angled face of the input light conduit (39).

Figure 7F:
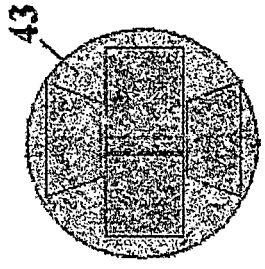
Figure 7E:
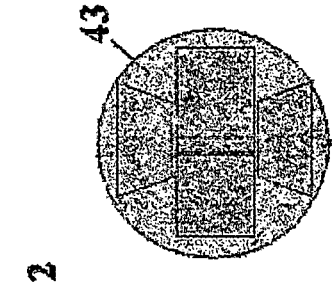
Figure 7D:
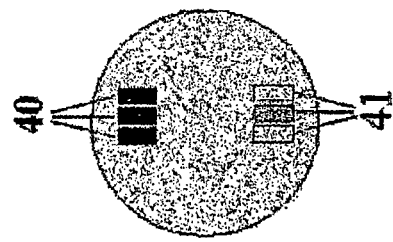

FIGS. 7D, 7E and 7F illustrate that in the transmission mode, there is an option to use a multiplicity of LED source components 40 in close proximity with a near-common light path. The system can utilize a comparable multiplicity of detectors 41 (or less) dependent on the final beam path and divergence through the optical structure.

FIG. 8A illustrates an embodiment wherein the fiber optics is mounted on a precision-drilled plate (or mandrel) 45. The plate 45 matches the cross-section of the sensor probe optical element (44) and provides a means for precise and rep ensuring that the optical path of the beam into the sample optical element is aligned optimally relative to the internal reflection surfaces. The mounting plate 45 is keyed to sensor probe optical element 44 by a step 44a in the optical element and a matching step 45a in the plate. This can be of the form of a notch or slot, cut or molded in the sensor probe optical element 44, which aligns to a key in the mounting plate 45. This enables the removal of the sensor probe 44 for cleaning and/or replacement in the event of contamination or damage.

As noted above, the fiber mounting plate will provide a means to obtain accurate fiber placement and also accurate and reproducible beam alignment through the sensor tip. The latter is essential for maintaining sensor calibration and for inter-sensor calibration. Preferably, each sensor will conform to a single calibration format. Minor coefficient modifications can be used to tune sensors in the event that the calibration transfer does not provide the desired measurement accuracy. The on-board data handling within the sensor can handle this tuning function, if required.

Additional optics are included at the mounting point of the fiber and the plate. These optics are close-coupled with the end of the fiber(s) and provide a means to focus or collimate the beam. This is essential in cases where the beam passage through the optical element must be optimized in terms of illumination (entrance) and beam collection (exit). If such optics are not used, there is a large divergence angle of light from the source, and little enters a first of optical fibers 46, used to supply light to the sensor probe. Further, light returning in a second of the optical fibers 46 to the detector also diverges over a large angle. The internal reflection measurement is highly angle dependent. Thus, in the absence of collimation optics for the source, and collection optics for the detector(s), the efficiency and optical integrity of the internal reflection device is adversely affected, and measurement accuracy may be significantly impaired. For low-cost applications, the use of simple plastic optics will be considered.

For most applications each light path will form a fiber pair, hence two opposing points will be drilled into the mounting plate . . . one for illumination and one for collection. As exemplified in FIGS. 8B and 8C, exception are considered for light scattering applications where three fibers may be included (one illuminator and two collectors). This latter configuration will not be required for normal soot measurements. The system can involve multiple light paths. This may be used for the soot sensor when a multi-faceted sample head is in use. Multiple wavelength measurements are considered to be a very important feature of this device, even for soot measurements, because most analyses of used lubricant systems produce non-linear responses. The use of multiple wavelength can help to provide linearization of such measurements. FIG. 8B illustrates a sensor 47 with a remote electronics module 48 (within the sensor) with optical fiber couplings 48a. FIG. 8C illustrates a remote electronics module 49 (within the sensor) with optical fiber couplings 48a and multi-wavelength sensing (two shown).

As shown in FIGS. 9A to 9E, the placement of the opto-electronics and the optical sensing structure may require modification dependent of the temperature of the system being monitored. In the simplest implementation, the opto-electronics can be close-coupled to the optical sensing structure (FIG. 9A, 50). If, as in most practical implementations, for ambient temperature reasons, it is necessary to separate these by an air gap (FIG. 9B or FIG. 9C) or an optical conduit or an insulating layer 62 (FIG. 9D), imaging elements, such as (52) of FIG. 9B, in the form of, for example, small focusing lenses should be employed, for the reasons set forth above.

The final packaging of the optical structure and the opto-electronics is dependent on the application and the cost targets for the final package. The enclosure (54 and 57) may comprise a single molded or extruded component for low-cost, disposable implementations. In other cases where the sensor may be re-used, and there is the need to gain access to the internal components after manufacture, then a fabrication containing two or more enclosure components will be used. In this case, attention is paid to the nature of the seal between the enclosure and the optical structure. A captive o-ring seal 55 is shown as an example in FIGS. 9C and 9D, but alternative methods can be adopted, dependent on the enclosure design, the construction materials, and the format of the optical structure. The enclosure can be tailored to high temperature applications by providing internal thermal insulation (62) and cooling fins 61 on the exterior surface of enclosure 57. For light transmission modes of operation, especially for low-cost implementations, the use of lower cost, low refractive index optics will require the use of a reflective surface or layer (60) as shown in FIG. 9E. In the final implementation this will require protection from the flowing stream, and this is accomplished by a shrouded enclosure (59) where the cover provides a seal around the reflective layer (60).

EXAMPLES AND APPLICATIONS

In the embodiments of the invention described herein, the focus is on functional fluid monitoring in automotive, vehicular, and static and dynamic motorized systems that may include engines (combustion, reciprocating, turbines, etc.), motors (electric, hydraulic, pneumatic, etc.), hydraulics, transmissions, gearboxes and differentials, cooling systems (including heat-exchangers and fluid-cooled metalworking, cutting and roller systems), battery and power cell fluids.

Example applications include the following:
d) the monitoring of soot in diesel engine lubricating oils,
e) the monitoring of oxidation/acidity in transmission and other lubricating oils,
f) the measurement of oil condition in gasoline and natural gas-fired engines based on the formation of oxidation and nitro-oxidation products,
g) the measurement of dispersed water (elevated levels) in hydraulic and lubrication oil systems,
h) the measurement of turbidity, which can result from water, air entrainment and/or particulates or other insoluble materials in functional fluids,
i) the measurement of coolant condition, based on color and turbidity,
j) the measurement of marker materials for fluid compatibility, usage and/or condition (color markers added to indicate chemical changes), k) the monitoring of battery acid condition (acid strength), based on a color indicator, etc.

Details of example implementations for specific areas of application:

The Monitoring of Soot in Diesel Engine Oils During Service:

A sensor comprising an internal reflection optical structure (the three-reflection version is standard) with a medium to low refractive index (approx. 1.8) in combination with a NIR Source-detector pair is the preferred embodiment for the soot monitoring application. The use of the longer wavelength (940 nm) LED will provide optimum sensitivity for the measurement of soot in the 0.5% to 10% range of concentrations. The use of a secondary detector channel with the balancing electronics will provide a stable, temperature independent output. Furthermore, it provides a direct output of sample absorption that can be correlated to soot concentration. The sensor is designed for this application as a low cost device, and as such it is packaged in a molded or extruded plastic enclosure, thereby making it a potentially disposable element. The benefits of using the NIR LED-detector pair, besides the issues of sensitivity (of the silicon detector), the cost, and the low energy consumption, are that in the measurement region, with the measurement mode employed, there are essentially no interferences to the measurement . . . there are no other significant absorptions in the spectral region for the internal reflectance mode of measurement. The benefit of the multifaceted design is that there is the option to use a dual-facet system, featuring different facet angles, that can extend the dynamic range of the measurements.

The monitoring of oxidation and nitration products in gasoline and gas-fired engines: It has been satisfactorily demonstrated that the optical spectrum can model and trend both oxidation and nitro-oxidation if multiple wavelengths are monitored in the visible and short-wave NIR regions. As the oil oxidizes and degrades, extended double bond structures are formed as part of aldol condensations that take place in the degradation pathway. These materials eventually become the insoluble organic sludge that separates from the oil after extended use. As the extended double-bond structures form, the absorption wavelength of these materials shifts to the red end of the spectrum, and eventually into the short-wave NIR. They may be tracked by monitoring the visible (green, yellow, red) and the NIR wavelengths. Also, the formation nitro components, from the NOx components may also be tracked in the visible.

The proposed embodiment of the sensor for this application is the optical transmission head, with a multiple LED configuration. In this case, the LED options could include a blue LED, a tri-state (green-yellow-red) LED and a short-wave NIR LED (such as the 880 nm). While the application could be well-suited for luxury automobiles, it might be more appropriate in lightweight trucks, including delivery trucks, and natural gas-powered transportation, such as buses. In either case, a low-cost option would be considered, and as in the case of the soot sensor, a single piece, extrusion or mold may be the preferred form for the enclosure. The opto-electronics would include the reference channel to provide thermal compensation and the direct output of sample absorption, for each channel monitored.

The Monitoring of Oxidation and Acid Number in Automatic Transmissions:

The red dye used in Dexron automatic transmission fluids can be demonstrated to act as an acid-base indicator, reflecting the condition and the acidity of the fluid during use. The acid number of tansmissions used in buses is an issue relative to warranty claims. An on-board sensor capable of modeling acid value based on the visible monitoring of the dye can provide an early warning to unacceptable acid numbers (relative to warranty). A sensor configured in a similar manner to the oxidation sensor described above is expected to be adequate, but probably without the need for the NIR channel.

What is claimed is:

1. An optical spectral sensing device, for determining properties of a sample, said device comprising:
   an integrated solid-state source and solid-state detector package,
   an optical structure with a substantially conical cross-section, for contacting said sample material;
   coupling apparatus for coupling said integrated solid-state source and solid-state detector to said optical structure; and
   integrated electronics for providing energy for said source and for receiving a signal generated by said detector in response to energy coupled to said detector by said coupling apparatus, said integrated electronics providing direct output of sample properties of said sample.

2. The device of claim 1, wherein said optical structure is formed in configurations that allow for at least one of internal reflectance when a sample is in contact with an external surface of the structure, or transmittance, or fluorescence or light scattering measurements of a sample in a channel in the structure.

3. The device of claim 1, wherein said optical structure is fabricated from a glass or plastic that can be machined, polished or molded to provide a circular base with either a conical cross-section in the form of a cone with an apex, or a truncated cone.

4. The device of claim 1, further comprising opposing flat facet surfaces between which energy is reflected.

5. The device of claim 4, wherein when a plurality of faceted surface pairs exists, the angles of the facets for the individual pairs may be different to facilitate angle tuning of the optical structure.

6. The device of claim 3, further comprising a cylindrical base, wherein the cylindrical base facilitates sealing, and wherein if said cylindrical base is formed as an extended base, said cylindrical base functions as said coupling apparatus.

7. The device of claim 1, wherein said optical structure has more than one set of tuned facet pairs between which light is reflected, thereby extending dynamic range for measurements of said sample.

8. The device of claim 1, wherein said optical structure is comprised of a glass or a plastic having a refractive index to match the measurement requirements of a selected application.

9. The device of claim 1, wherein said optical structure includes channels, slots or cavities that allow the sample to pass between two opposing optical faces formed in the optical structure, thereby enabling measurements by at least one of optical transmission or optical light scattering.

10. The device of claim 9, wherein in the optical transmission mode energy passes a first face of the optical structure and into the sample, traverses the sample and re-enters the optical structure at an opposing face.

11. The device of claim 9, wherein in an optical scattering mode, energy passes a first face of the optical structure into the sample, interacts with the sample, and any scattering that results from this interaction is observed through a base of a cavity in the optical structure, said energy propagating at 90° with respect to normal passage of energy through the sample.

12. The device of claim 1, wherein said source and detector are located at matched positions to provide an optimum passage of energy through said optical structure utilizing at least one of internal reflection, light transmission and light scattering.

13. The device of claim 1, wherein in the case of scattering by the sample or fluorescence of the sample, the detector is mounted in a central position to receive scattered or fluorescent energy.

14. The device of claim 12, wherein the integration of the source and detector constitutes the formation of an integrated internal sensing module to complement the optical structure.

15. The device of claim 1, having an integrated internal sensing module containing said solid state source and said solid state detector package, wherein said source comprises a solid-state device, primarily designed to emit light or energy with a maximum energy at a center wavelength defined by the device.

16. The device of claim 1, wherein said optical structure, and said package are housed within an enclosure that protects internal components from the operating environment and the sample.

17. The device of claim 16, wherein said enclosure is fabricated from a single piece of material in the form of a molding or extrusion, or is fabricated from two or more parts to provide a device that can be disassembled for servicing.

18. The device of claim 17, wherein said device is disposable.

19. The device of claim 16, wherein said, enclosure is constructed of a thermally insulating material to reduce the internal heat within the sensor, or said enclosure is structured externally to include cooling fins or structures to dissipate heat from the device.

20. An integrated sensing module having a source and a principal detector comprising a solid-state device either matched directly in spectral response to said source, or capable of responding to wavelengths over a broad spectral range from one or more sources, sensitive in spectral regions of mid-to long wavelength near infrared (1100 nm to 2500 nm) and mid-infrared (2.5 µm to 25 µm, 2.500 nm to 25000 nm), wherein said detector is located in either a primary location in the module for the detection of source radiation from internal reflection or transmission measurements, or a secondary location at the center or close to the center of the module, for the detection of radiation from fluorescence or from energy scattered from a fluid from under study.

21. The sensing module of claim 20, further comprising an optical system including a reference detector arranged to accept energy directly from the source.

22. The sensing module of claim 20, further comprising an optical structure for coming into contact with a sample to be measured, and a base containing said source and said detector, said optical structure and said base being mechanically keyed to one another to assure alignment between said optical structure and said source and detector on said base.

23. The sensing module of claim 21, wherein said reference detector operates with balancing electronics to reduce or eliminate temperature dependent changes in performance of said optical system.

24. The sensing module of claim 22, further comprising an optical system including a reference detector arranged to accept energy directly from the source, wherein said reference detector provides a ratio of energy detected by said principal detector and energy obtained from the reference detector, thereby providing a direct measure of the energy absorbed by the sample and said optical structure.

25. The sensing module of claim 20, wherein said optical system includes more than one source-detector pair.

26. The sensing module of claim 25, wherein sources are adjacent to each other or share a common optical path through a main optical structure, whereby one or more detectors mounted in matched positions on the sensing module detects energy passing through the main optical structure.

27. The sensing module of claim 20, further comprising a conical optical stucture for coming into contact with a sample to be measured, including more than one source-detector pair, the sources in said source-detector pairs being in different locations and taking different paths through said conical optical structure, as defined by different locations on said conical optical structure or by different reflections between facet pairs on the conical optical structure, so that the sources utilize different detectors in locations matched to respective source location.

28. The sensing module of claim 26, wherein wavelengths emitted by the sources form a plurality of wavelengths thereby enabling more than one analysis to be performed, or where analysis can be performed in the event that a condition being monitored provides different independent responses at different wavelengths, said sensor module providing an output for either multiple components or measurement of a complex condition by use of modeling techniques.

29. The sensing module of claim 20, further comprising an optical structure; and additional optics, in the form of small lenses or light conduits or optical fibers, to improve optical interfacing between the source and detector devices and the optical structure, thereby improving measurement efficiency and accuracy.

30. The sensing module of claim 29, wherein the sensing module is located away from the optical structure.

31. The sensing module of claim 30, further comprising supplemental thermal insulation to reduce impact of heat on the sensing module.

32. The sensing module of claim 20, wherein the source is a light emitting diode and output from the light emitting diode is modulated and regulated under thermal management to ensure an extended operational lifetime for the light emitting diode.

33. The sensing module of claim 20, further comprising a processor for processing the signal produced from the detector.

34. The sensing module of claim 33, further comprising built-in or downloaded calibration coefficients for said processor.

35. The sensing module of claim 33, wherein said processor further comprises at least one of:
   a computation means for performing computations including concentration calculations;
   processing of intelligent sensor outputs; and
   support for standard data formats, standard protocols and standard forms of communications, including serial and bus-oriented communications formats.

36. The sensing module of claim 27 wherein the wavelengths emitted by the solid-state sources form a plurality of wavelengths thereby enabling more than one analysis to be performed, or where a more complex analysis can be performed in the event that a condition being monitored provides different independent responses at different wavelengths, said sensor module providing an output for either multiple components or the measurement of a complex condition by use of modeling techniques.

* * * * *